United States Patent [19]

Finch-Savage

[11] Patent Number: 4,905,411
[45] Date of Patent: Mar. 6, 1990

[54] SEED TREATMENT

[75] Inventor: William E. Finch-Savage, Kineton, England

[73] Assignee: National Research Development Corporation, London, England

[21] Appl. No.: 300,686

[22] Filed: Jan. 19, 1989

Related U.S. Application Data

[63] Continuation of Ser. No. 229,459, Aug. 8, 1988, abandoned, which is a continuation of Ser. No. 863,949, May 16, 1986, abandoned.

[30] Foreign Application Priority Data

| Date | Country | Number |
|---|---|---|
| May 16, 1985 [GB] | United Kingdom | 8512391 |
| May 17, 1985 [GB] | United Kingdom | 8512586 |
| Sep. 23, 1985 [GB] | United Kingdom | 8523448 |
| Oct. 31, 1985 [GB] | United Kingdom | 8526823 |

[51] Int. Cl.$^4$ .............................................. A01C 1/00
[52] U.S. Cl. ..................................... 47/58; 47/DIG. 9
[58] Field of Search ............................. 47/58, DIG. 9; 111/6-7

[56] References Cited

U.S. PATENT DOCUMENTS

| | | | |
|---|---|---|---|
| 1,756,497 | 4/1930 | Warren | 47/58 |
| 2,789,398 | 4/1957 | Willett | 47/58 |
| 2,954,643 | 10/1960 | Porter et al. | 47/58 |
| 3,130,694 | 4/1964 | Gatzke | 111/7 |
| 3,950,892 | 4/1976 | Simkin | 47/58 |
| 4,315,380 | 2/1982 | Davidson | 47/58 |
| 4,467,560 | 8/1984 | Simak | 47/58 |
| 4,631,860 | 12/1986 | Broughton | 47/58 |

FOREIGN PATENT DOCUMENTS

| | | |
|---|---|---|
| 0030575 | 6/1981 | European Pat. Off. |
| 0062383 | 10/1982 | European Pat. Off. |
| 0171553 | 2/1986 | European Pat. Off. |
| 1964001 | 6/1971 | Fed. Rep. of Germany |
| 2736407 | 2/1979 | Fed. Rep. of Germany |
| 2270773 | 12/1975 | France |
| 1136758 | 1/1985 | U.S.S.R. |
| 268291 | 8/1927 | United Kingdom |
| 926856 | 5/1963 | United Kingdom |
| 1470133 | 4/1977 | United Kingdom |
| 1492438 | 11/1977 | United Kingdom |
| 1535926 | 12/1978 | United Kingdom |
| 1583148 | 1/1981 | United Kingdom |
| 2064941 | 6/1981 | United Kingdom |

OTHER PUBLICATIONS

*Journal of Experimental Botany*, (1982), vol. 33, pp. 1045–1047, "Desiccation-Tolerant and Desiccation-Intolerant Stages During the Development and *Germination of Phaseoulus Vulgaris Seeds*", J. Dasgupta, et al.
*New Phytologist*, (1977), vol. 78, pp. 349–359, "Seed Activation and Seed Germination Under Moisture Stress", T. W. Hegarty.
*Soil Conservation Journal*, (1974), vol. 29, pp. 28–41, "The Effect of Water Potential on the Germination Behaviour of Several Warm Season Grass Species, with Special Reference to Cracking Black Clay Soils", L. A. Watt.
*Canadian Journal of Botany*, (1971), vol. 50, pp. 105–108, "Effect of Treatments Given to Grain, on the Growth of Wheat Roots Under Drought Conditions", M. S. Carceller et al.
*Arid Zone Research News Letter*, (1962), vol. 16, pp. 271–274, "La 'Reviviscence' Ou Aptitude a L'Anhydrobiose' Et Ses Variations Naturelles et Experimentales Chez Les Plantules" C. Hubac.
*Field Crop Abstracts*, (1962), vol. 15, pp. 1–6, "Pre-Sowing Hardening of Plants to Drought", L. H. May et al.
*Agronomy Journal*, (1979), vol. 71, pp. 783–786, "Tolerance of Desiccation in Germinating Seeds of Crested Wheatgrass and Russian Wildrye", Hassanyar et al.
*Seed Science & Technology*, (1975), vol. 3, pp. 881–888, "Invigoration of Seeds?" W. Heydecker et al.
*Conference Malvern Ref Book*, (1980) pp. 70–85, "Seed Physiology", S. Matthews.
*Plant, Cell and Environment*, (1978), vol. 1, pp. 101–119, "The Physiology of Seed Hydration and Dehydration, and the Relation Between Water Stress and the Control of Germination: A Review", T. W. Hegarty.
*Plant Physiology*, (1979), vol. 64, pp. 822–827, "Control of Seed Germination by Abscisic Acid", P. Schopfer et al.
*Plant Physiology*, vol. 76, pp. 155–160, "Control of Seed Germination by Abscisic Acid", P. Schopfer et al.
*Can. J. Bot.*, (1980), vol. 58, pp. 471–475, "Effects of Dehydration Treatments on Germination, Seedling Vigour, and Cytoplasmic Leakage in Wild Oats and Birdsfoot Trefoil", B. D. McKersie et al.
*Grower*, (1984) pp. 15 & 17, "Modules".

(List continued on next page.)

*Primary Examiner*—Robert E. Bagwill
*Attorney, Agent, or Firm*—Oblon, Spivak, McClelland, Maier & Neustadt

[57] ABSTRACT

The invention relates to germinated seeds of a plant species other than one characterised by a seminal root system, for example seeds of small seeded vegetables, the seeds having emerged radicles and a moisture content at which radicle development is suspended without loss of seed viability. Seeds may be subjected to a treatment which includes imbibing the seeds to a stage where radicles have emerged in a substantial proportion thereof and drying in a two stage process the first stage comprising drying to a moisture content at which individual seeds are separable and free flowing and the second stage comprising drying in an atmosphere of fairly high relative humidity such as 70% to 90% at a temperature in the range 20° to 30° C.

Seeds treated according to the invention have advantageous properties in terms of storage and subsequent development on exposure to a suitable environment.

11 Claims, No Drawings

OTHER PUBLICATIONS

*New Phytol,* (1971), vol. 70, pp. 135–142, "The Effect of Hydration–Dehydration on Seed Germination", Berrie et al.

*NVRS Annual Report* (1983), Finch–Savage and McQuistan.

*Cryobiology,* (1983), vol. 20, pp. 487–503, "Drought and Freezing Tolerance and Adaptation in Plants: Some Evidence of Near Equivalences", D. Siminovitch et al.

*Plant Physiol,* (1982), vol. 69, pp. 250–255, "Twenty-Four-Hour Induction of Freezing and Drought Tolerance in Plumules of Winter Rye Seedlings by Desciccation Stress at Room Temperature in the Dark", D. Siminovitch et al.

*Agronomy Journal,* (1979), vol. 71, pp. 783–786, "Tolerance of Desiccation in Germinating Seeds of Crested Wheatgrass and Russian Wildrye", Hassanyar et al.

*Physiologia Plantarum,* (1962), vol. 15, pp. 43–46, "Presowing Treatments and Their Relation to Growth and to Drought, Frost & Heat Resistance", Y. Waisel.

*Annals of Botany N.S.,* (1940), vol. XIV, pp. 79–89, "Changes in the Drought Resistance of Wheat Seedlings During Germination", F. L. Milthorpe.

Fluid Drilling, Ltd., "Variations on the Basic Principles".

*Gartenbau,* (1986), vol. 1, pp. 3–5, "Effektivitat Der Saatgutvorbehandlung im Produktionsbetrieb und Einzelkornaussaat zur Jungpflanzenanzuchi", E. Walter.

*Sveriges Shogsvadsforbunds Tidskrift,* (1985), vol. 1, pp. 57–63, "Forgrodda Fron", M. Hagner.

SEED TREATMENT

This application is a continuation of application Ser. No. 229,459 filed on Aug. 8, 1988, which is a continuation of Ser. No. 863,949, filed on May 16, 1986, both now abandoned.

BACKGROUND OF THE INVENTION

1. Field of the Invention

This invention relates to methods for treating seeds for planting and to treated seeds having improved properties.

DISCUSSION OF THE BACKGROUND

The establishment of certain types of plant from seed in both the field and the glasshouse is made difficult as a result of variable seed quality and variations in the environmental conditions during germination. In order to overcome some of these difficulties the so-called fluid drilling technique has been developed in which previously germinated seed is sown in a protective gel. However, most pregerminated seeds begin to deteriorate soon after germination even if kept cool and principally for this reason it has not been practicable for seed suppliers to prepare large quantities of germinated seed for distribution to their customers as and when required. instead, the farmer himself has had to prepare the seeds for drilling and this has involved him in the extra cost of germination equipment and operation.

Once sufficient seed has been germinated then drilling may not be unduly delayed if the seed is not to deteriorate. This is particularly troublesome in bad weather or at times of mechanical breakdown of drilling equipment. In addition, fluid drilling does not allow seeds to be planted one by one and the seed-to-seed spacing cannot be accurately controlled. Moreover, to prevent radicle damage and other problems the radicle at sowing should preferably not be much more than 3 mm long. But because there is a wide variation in germination times within seed lots, only a proportion of the seeds will be adequately germinated when the most advanced have radicles of the preferred length. The full potential of sowing germinated seed is therefore not being achieved.

It is the object of the present invention to provide seeds for sowing from which plants are readily established and which are less subject to the above-mentioned disadvantages which have previously been associated with sowing germinated seed.

The invention is widely applicable to species in which successful and normal growth of the primary root is essential for the survival and health of the plant. These species are categorised in the Handbook for Seedling Evaluation, J. Bekendam and R. Grob, ISTA, Zurich, Switzerland 1979 on pages 28, 29 (Page 29, group 1, primary root essential). In addition the invention may be applicable to species in group 2 as defined on page 29 of the above-mentioned reference (secondary roots taken into account). The species of groups 1 and 2 together can be characterised as not having a seminal root system in which an equal secondary root can successfully replace the primary root if it fails to become properly established. These species are exemplified by a representative index at pages 122-126. The Handbook for Seedling Evaluation is an authoritative publication generally used in the seed trade throughout the world and its contents are incorporated herein by reference.

It has now surprisingly been found that seeds of the kind for which the above-mentioned difficulties are encountered may be germinated to the stage of emergence of the radicles and then treated to reduce their moisture content in order to arrest further development of the radicle whilst maintaining the viability of the potential seedling.

Many reports have appeared in the scientific literature on the effect upon seeds or seedlings of so-called "desiccation stress" in inducing a degree of tolerance in the developing plant to drought and freezing conditions. These treatments involve cycles of wetting and drying before the seeds have germinated. For example, early work of this kind has been summarised by May et al (1962 Field Crop Abstracts 15, 1-6) who concluded that the stage of development of the embryo was critical in relation to susceptibility to drying. Some studies have also been made on seeds with emergent radicles, e.g. Waisel (1962 Physiologia Plantarum 15, 43-46), Carceller and Soriano (1971 Canadian Journal of Botany 50, 105-108) and Milthorpe (1950 Annals of Botany 14, 79-87) but these were concerned with cereals and described severe treatments from which if seedlings survived they may have done so because of their seminal root system. There are also other academic studies. for example the papers by Siminovitch and Cloutier (1982 Plant Physiology 69, 250-255 and 1983 Cryobiology 20, 487-503) which are typical of many in that they are directed mainly at cereals and are more concerned with the effect of the treatment on the plant shoots (plumules) than on the plant roots. Similarly, published work on the effect of desiccation stress on the seeds of small-seeded and other vegetable crops has in general described very severe and often lethal conditions of desiccation and no conclusions of practical value have so far emerged which would provide a solution of the problems to which the present invention is addressed. Moreover the drying of seeds after germination is generally contraindicated in these papers, for example, Berrie and Drennan, (1971 new Phytologist 70, 135-142), Dasgupta, Bewley and Yeung, (1982 Journal of Experimental Botany 33, 1045-1057) and Hegarty, (1977 New Phytologist 78, 349-359).

SUMMARY OF THE INVENTION

The present invention provides germinated seeds of a plant species other than one characterised by a seminal root system, said seeds having emerged radicles and a moisture content at which radicle development is suspended without loss of seed viability.

The invention also provides a process for the treatment of seeds of a plant species other than one characterised by a seminal root system which comprises imbibing the seeds to a stage where radicles have emerged in a substantial proportion thereof and drying the seeds under conditions and to a moisture content which suspends radicle development but does not result in loss of viability.

In appropriate cases the seeds may be selected, for example, prior to drying, on the basis of their germination characteristics. Drying may be carried out in two stages the first stage comprising drying the seed to a moisture content at which individual seeds are separable and free flowing and the second stage comprising further drying the seed under conditions and to a moisture content which suspends radicle development but does not result in loss of viability. The seed may be coated at an appropriate stage following germination to facilitate handling and sowing without damage.

DETAILED DESCRIPTION OF THE PREFERRED EMBODIMENTS

Examples of species to which the invention is applicable include species of the genus Brassica, Allium, and Beta.

In one particularly advantageous embodiment the invention can be applied to the seeds of small seeded vegetables.

Examples of species to which the invention has been successfully applied are:

*Allium cepa*
*Allium porum*
*Brassica oleracea*
*Brassica campestris*
*Brassica napus*
*Beta vulgaris*
*Daucus carota*
*Lycopersicon esculentum*

Further examples of species to which the present invention is applicable include the following:

Compositae
*Carthamus tinctorius*
*Heliantus annuus*
*Lactuca sativa*
Chicorium spp.
Brassicas
*Brassica juncea*
*Brassica nigra*
*Brassica carinata*
Cruciferae
*Raphanus sativus*
*Sinapsis alba*
Cucurbitaceae
*Cucumis sativus*
*Cucumis melo*
*Citrullus lanatus*
*Cucurbita pepo*
*Cucurbita siceraria*
*Cucurbita mixta*
*Cucurbita moschata*
*Cucurbita maxima*
*Cucurbita ficifolia*
Gramineae - Oryzeae
*Oryza sativa*
Gramineae - Andropogoneae
Saccharum
Gramineae - Maydeae
*Zea mays*
Leguminosea - Papilionatae
*Phaseolus vulgaris*
*Phaseolus coccineus*
*Pisum sativum*
*Vicia faba*
Linaceae
*Linum usitatisimum*
Malvaceae
Gossypium spp. (including *hirsutum* and *barbadense*)
Moraceae
*Cannabis sativa*
Roseceae
Fragaria spp. (including *ananassa*)
Solanaceae
Capsicum spp. (including *annuum*)
*Nicotiana tabacum*
*Solanum melongona*
Chenopodicaceae
*Spinacla oleracea*
Liliaceae -continued

*Asparagus officinalis*
Umbelliferae
*Apium graveolens*
*Pastinaea sativa*
*Petroselinum crispum*
Pinus
Pinus spp. including:
*Pinus elliottii*
*Pinus radiata*
*Pinus resinosa*
*Pinus sylvestris*
*Pinus taeda*
Picea
Picea spp. including:
*Picea abies*
*Picea glauca*
*Picea mariana*
*Picea obovata*
*Picea sitchensis*
Larix
*Larix decidua*
*Larix kaempferi*
Pseudotsuga
*Pseudotsuga menziesii*
Sequoia
*Sequoia semperyirens*

As used herein the term "viable" refers to a seed which produces a seedling capable of developing into a mature plant. Viability in a seed lot may conveniently be assessed experimentally by the method laid down by the International Rules for Seed Testing (Seed Science and Technology 4, 40–43, (1976)).

Seed treated in accordance with the present invention with or without coating, may be sown in any conventional manner which does not damage the seed. Preferably the seed is sown with conventional machinery for sowing dry seed although seeds treated according to the invention may also be sown by fluid drilling. The seed according to the invention continues normal development on exposure to a suitable environment after sowing. In those cases where seeds treated according to the invention can be sown in conventional machinery, precision spacing of the individual seeds is possible in contrast to fluid drilling techniques. Since the seed is already germinated the invention provides the potential, with appropriate selection after germination, for sowing completely germinated seed which develops quickly and uniformly after sowing. The invention also provides seed having sufficient stability on storage for germination and drying to be carried out by a seed processor prior to distribution for sowing by the end user.

The processing of seed in accordance with this invention involves subjecting seed in quantity to successive treatment stages according to the following scheme.

Imbibition and germination

A batch of dry seed may be treated in a water treatment bath until sufficient water is imbibed to induce germination. The bath is preferably aerated and run as a continuous flow system to remove leached out substances and avoid contamination. The conditions of time and temperature of water treatment may be sufficient to cause germination to proceed to the stage of radicle emergence in a high proportion of the seeds. The duration of treatment will vary with the type of seed and information concerning germination time is widely available for a wide variety of seeds.

In a variant of this procedure a shorter time of water treatment is used and excess water is removed from imbibed seeds before the radicles appear, the latter being allowed to take place in the same or at a different location in the absence of bulk fluid. In either case this stage of treatment is discontinued when the radicles emerging from a substantial proportion of the seed are still of very short length. For example, in the case of cabbage seeds, for the best results, the radicles should not be more than 1 or 2 mm long before the next stage is commenced while for onion seeds the corresponding range is from 1 to 3 mm, say. At this length the radicles are less likely to be damaged during handling in this or a subsequent stage.

Seed selection

Seed selection is an optional feature of the process according to the invention in that it may not be necessary or economic in the case of certain crops for example rape and sugar beet. Seed may also be subjected to physiological pre-treatments such as osmotic seed priming, cold treatments, or plant growth regulator soaks to increase efficiency and uniformity of germination.

The basis of selection of the desired seed may be chosen according to various criteria. The proportion of seed which has not germinated to the desired extent at the conclusion of the first stage in the water bath should be separated. Selection of germinated from ungerminated seeds may be carried out using known flotation techniques in which germinated seeds rise to the top of the flotation tank by virtue of their lower specific gravity while ungerminated seed sink to the bottom. Further details of this technique can be found in Taylor et al., HortScience 13, 481–482 (1978), Taylor et al, HortScience 14 412 (Abs) (1979), Taylor et al, HortScience 16, 198–200 (1981).

Another separation technique has been described in UK specification 1,470,133 in which seeds are germinated on the surface of water in a tank and as the radicle emerges it breaks through the surface and grows down beneath the surface of the water. A series of alternately sucking and blowing probes passing beneath the water suck the germinated seeds below the surface by the radicle and seeds are then collected off the bottom of the tank.

Techniques can be refined in order to be even more selective. Thus they can be used to separate those individual seeds which have been the first to germinate; recent research has shown that this latter type of seed tends to be the most vigorous and has the greatest viability (Finch-Savage Annals of Applied Biology 108, 441–444 (1986)). The non-germinated seeds may be recycled and further treated in order to induce germination. If desired this sequential approach may be continued in order to recover the maximum yield of germinable seeds from the original batch of seeds. The lultimate objective, in all cases, is to produce seed lots containing as near as possible to 100% viable seeds capable of rapid and predictable seedling development.

Drying

The drying of the germinated seed according to this invention is preferably carried out in two stages which can be termed preliminary and final drying.

(a) Preliminary drying

The primary purpose of this stage of drying is to remove surface moisture which causes the seeds to agglomerate. It is therefore characterised by vigorous conditions of relatively short duration which cause the mass of seeds to become free-flowing and to retain this property in later stages of treatment. These conditions of preliminary drying may incidentally slightly reduce the internal moisture content of the seeds but not sufficiently to completely arrest radicle growth. By way of example, seeds are removed from the aerated water bath once germination has begun, and germinated seeds are selected if appropriate and then centrifuged to remove excess water typically at about $70 \times g$. They may then be subjected to an air flow, for example, at around $2.6 \text{ m sec}^{-1}$ with an air temperature of about 20° C. and relative humidity of about 50% until sufficient moisture has been removed for individual seeds not to adhere to one another in the subsequent drying stage.

(b) Final drying

The object of this drying phase is to arrest development of the radicles at lengths of the order indicated above and to make them permanently free-flowing in the absence of the further application of water. In this form the seed may be more readily coated if required and converted into the rounded form necessary for accurate sowing in many conventional dry seed drills. The moisture content to which the seeds are typically dried causes radicle development to be suspended but the conditions of drying are such as to preserve viability and enable normal development to be resumed in the soil. The term "moisture content" as used throughout the specification refers to the moisture content of the seeds calculated on a fresh weight basis. Rules for determining moisture content as above defined have been promulgated by the International Seed Testing Association in Seed Science and Technology, 4, 40–43 (1976).

The process according to the invention should be carried out under such conditions and the seeds produced should have moisture levels such that a seed lot which has been treated contains as high a proportion as possible of viable seed. In many cases the process can be carried out without any significant loss of viability in the seed lot, i.e. there is no significant difference in the proportion of viable seeds before and after treatment. The proportion of viable seeds which is expected in lots of natural seeds varies from one species to another and minimum proportions of viable seeds in seed lots offered for sale are the subject of regulations in many countries. In some cases some reduction in the proportion of viable seeds might be tolerated as between seed before and after treatment according to the invention.

Conveniently, the moisture content of the seeds is reduced to 45% or less and preferably to below 40% to check seed development. For onion seed and cabbage seed, for example, further radicle growth will be substantially prevented at moisture contents of below 45%. The permissible subsequent storage time of the dried seed can be significantly increased, e.g. to one month or more, by reducing the moisture content of the seeds to around 35% or less and preferably 30% or less. The moisture content can with advantage be further reduced to around 20% or less, e.g. 15% being preferred. In some cases the moisture content can be reduced to levels typically present in commercially available natural seed.

The reduction of moisture content may be carried out by exposing the germinated seed to a drying atmosphere of fairly high relative humidity, e.g. in the range 70% to 90%. The best drying conditions for a particular species can readily be determined experimentally. However air at 80–85% relative humidity has been found to have wide applicability. Optimum drying temperaures are generally in the range 20°–30° C.

Some air movement is advantageous in the drying atmosphere to assist the evaporation of moisture from the seeds. The seeds can be spread in a single layer or may be arranged in a bed of 2 or 3 cm deep. Air is preferably made to flow through the bed at up to 0.4 m sec$^{-1}$ preferably 0.2–0.25 m sec$^{-1}$. The seeds are generally supported on a perforated support surface to facilitate air flow from all sides.

The drying times at a given temperature and relative humidity will depend on how the seeds are arranged and on the type of seed being treated.

Final drying may also be carried out by treating the germinated seed with a liquid medium which is physiologically inert and to which the germinated seeds are impermeable and which liquid medium has an osmotic strength such that moisture passes from the seeds to the liquid medium. The liquid medium is generally an aqueous solution of a suitable solute, the concentration of the solute being used to adjust the solution to the osmotic strength required to reduce the moisture content of the seeds. Examples of suitable solutes include polyethers, such as polyethylene glycol. The treatment may be carried out, for example, at ambient temperatures and the medium is preferably aerated during the moisture reduction treatment. The length of the treatment for a particular seed at a particular temperature will depend on the osmotic strength of the liquid medium and the moisture level desired in the seed. The liquid medium may be recycled, if necessary after ultrafiltration to remove low molecular weight materials derived from the seed and concentrate the high molecular weight solute.

Applying a seed coating

Application of a seed coating is an optional feature of the invention since some seeds which have been subjected to the final drying described above can be sown in some types of conventional machinery for sowing dry seed for example vacuum seeders and many can be sown by conventional fluid drilling techniques without further treatment.

The germinated seeds may be coated prior to the preliminary drying stage. Alternatively they may be coated at this stage either immediately following centrifuging or after or instead of application of the air flow. At this point the surface of the seeds will be moist. It is therefore possible to coat the seeds by rolling or otherwise dusting them in a dry mixture of absorbent gel powder and an inert substance such as talc, the already moist surface of the seeds being used to secure adherence of the coating material. Exposing the coated seed to an atmosphere of near 100% relative humidity followed by brief drying under ambient conditions will assist in securing the seed coat to the seed. The purpose of coating the seeds is to provide them with a protective surface which will guard them against damage. A thin coating may suffice for this purpose.

Alternatively, a coating may be applied to the seeds when the final drying step has been completed using low abrasion methods e.g. fluidised bed methods. It is important to avoid further drying of the seed during coating and it may be appropriate, for example, to carry out fluidised bed coating under conditions of temperature and relative humidity similar to those used for the final drying.

Initial coating may be followed by further coating in a conventional pan coater to form a pellet once the first coating has set.

Storage of dried seed

The seed treated according to the invention may be stored at near-zero temperatures, e.g. between about ±3° C. It has been found that seed having a moisture content of around 30% or so is usually best stored at near-zero temperatures slightly in excess of 0° C., e.g. at temperatures of around 1° C. It has been shown, for example, that cauliflower seed of about 30% moisture content can be stored in sealed containers at around 1° C. for a period of several weeks without significant loss of viability. Seeds having a moisture content of less than 30%, however, are generally best stored at slightly sub-zero temperatures, e.g. at around −3° C.

The reduction in moisture content which takes place in the treatment according to the invention may make the seed suitable for storage by deep freezing. For example, at moisture contents of 20% or less seed such as cabbage seed can generally be subjected to prolonged storage in a deep freeze (−18 to −20° C.) for periods of at least several months without any adverse effects on viability. This contrasts with the safe storage time for germinated cabbage seed by existing methods which is only 3 to 4 days.

One example of an apparatus suitable for treating seed by the method according to the invention comprises a seed-treatment chamber, a humidifier for maintaining the air of the seed-treatment chamber at a fairly high relative humidity, and a temperature-regulator for maintaining the temperature of the air of the seed-treatment chamber at the desired temperature. The humidity of the seed-treatment chamber might, for example, in small installations be controlled by use of an aqueous chemical solution of known concentration e.g. potassium hydroxide. In larger installations, however, the humidity may be controlled by means of a sensor-controlled humidifier and/or dehumidifier arrangement or other suitable air conditioning equipment. One or more fans or blowers may be added to provide air flow through the seeds.

A complete seed-treatment plant may further include, in one example, an aerated water tank, with a continual passage of water through the tank, for commencement of the germination process prior to transfer of the seeds to the seed-treatment chamber, a centrifuge device for removing surface water from the seeds prior to transfer and optionally a refrigerated storage chamber for storing treated seeds received from the seed-treatment chamber.

The invention is further illustrated by the following examples.

Example 1—Cabbage

1. Germination

Cabbage seeds (cv Hawke) were placed in nylon mesh bags in aerated water at a temperature of 20° C. The nylon mesh was wide enough to allow water movement but not sufficiently large to allow roots to grow through the bag. The flow of air was sufficient to both oxygenate the water and support the weight of the seeds. Water was constantly flushed through the system at a rate sufficient to provide at least one complete change of volume each 24 hours. The seeds were removed from the water after 16 to 18 hours. At this time about 45% of the seeds were germinated with radicle lengths up to 2.5 mm.

2. Selection

The seeds were removed from the nylon bags and sorted by hand to select those which had germinated and had a radicle length of between 1 and 2 mm.

3. Preliminary Drying

The selected seeds were centrifuged at 70×g for 40 seconds and subjected to a stream of air at 20° C. and 50% relative humidity (RH) with a speed of 1.6 m sec$^{-1}$ until fluidised, i.e. the seeds moved independently (1–2 minutes).

4a. Final Drying

The seeds were placed in a single layer on stainless steel mesh and subjected to a flow of air at 20° C. and 80±3% RH of 0.2 m sec$^{-1}$ for a period of about 7 hours. At the end of this period the moisture content of the seeds was 14% as measured in accordance with the rules of the International Seed Testing Association (Seed Science and Technology, 4, 40–43 (1976)). No loss of viability as compared to natural seed from the same batch was detected using the internationally accepted method laid down by the International Rules for Seed Testing (Seed Science and Technology, 4, 40–43, (1976)).

4b. Drying in Liquid Medium

Seeds treated according to 1.1 and 1.2 above were placed into an aerated aqueous solution of polyethylene glycol (molecular weight 6000) with an osmotic potential of −4.0 MPa for a period of 4 hours. At the end of this period the moisture content was 25%. No loss of viability was detected as compared to freshly germinated seed from the same batch.

5. Growth Tests

Growth of the dried seeds was investigated by the standard method of slope tests (Gray and Steckel, Annals of Applied Biology, 103, 327–334 (1983)). Seeds treated according to the invention (product of 1.4a above) and freshly germinated seed were placed on slopes and allowed to develop. Root and shoot lengths were measured 7 days later. No significant differences were detected between seed treated according to the invention and freshly germinated seed.

6. Storage

Seed treated according to the invention (product of 1.4a above) was stored in a domestic deep freeze (−18° to −20° C.) for 3 months. No loss of viability was detected as compared to freshly treated seed of the same batch.

7. Mechanical Sowing

Seed treated according to the invention (product of 1.4a above) was passed through a vacuum seeder of the type used for sowing seed into modules. The seeder operated in the conventional manner with the seed being agitated in a vibrating tray and transferred to the position required held to a probe by means of a vacuum. Following passage through the vacuum seeder no loss of viability was detected as compared to seed of the same batch which had not been passed through the seeder.

8. Preliminary Coating

Seeds treated according to 1.1 above were drained to remove excess water and then rolled in a finely ground mixture of Waterlock B-100 super absorbent polymer* and talc in a ratio of 1:10 by weight. The resulting coated seeds were placed in an atmosphere approaching 100% RH at room temperature (20° C.) for 1 hour. Seeds were then dried under ambient conditions (50% RH, 20° C.) for 15 minutes. Seeds coated in this way showed no loss of viability as compred to uncoated germinated seed.

(*Product of Grain Processing Corporation, Iowa, U.S.A.)

Example 2—Onion

Onion seeds (cv Hyper) were germinated, selected and dried by the method described in example 1.1, 1.2, 1.3 and 1.4a above except for the following differences. The treatment in aerated water was carried out for 4 days. Air speed in the preliminary drying stage was 1.25 m sec$^{-1}$ and in the final drying stage the air was at 20° C. and 85±3% RH. Final drying was carried out for 15 hours and the dried seeds had a moisture content of 15.9%. The dried seeds showed no loss of viability as compared to natural seed from the same batch.

Example 3—Sugar Beet

Sugar beet seeds were germinated, selected and dried as described in example 2 above except that the treatment in aerated water was carried out for 3 days and final drying was carried out for 7 hours and for 16 hours. After 7 hours the dried seeds had a moisture content of 18.2% and after 16 hours the dried seeds had a moisture content of 14.1%. Seeds dried in this way were sown with natural seed as a control into seed trays in a heated glasshouse (minimum night temperature 14° C., minimum day temperature 17° C.). The following results were obtained:

|  | % emergence | Time to 50% emergence (days) |
| --- | --- | --- |
| natural seeds | 93.1 | 6.5 |
| treated seeds | 100.1 | 4.5 |

Example 4—Brussel Sprouts

1. Seed Treatment

Brussel sprout seeds (cv Achilles) were germinated, selected and dried as described in example 2 above except that the treatment in aerated water was carried out for 24 hours and final drying was carried out for 6¼ hours. The dried seeds had a moisture content of 16.0% and showed no loss of viability as compared to freshly germinated seed from the same batch.

2. Seed Treatment Including Separation on Sucrose Gradients

Brussel sprout seeds (cv Achilles) were germinated and germinated seed separated by a method similar to that of Taylor et al., HortScience 16(2), 198–200 (1981)) using sucrose solutions of known specific gravity. Prior to germination the seeds were placed in a series of solutions having a range of specific gravities (8 solutions in the range 1.05 to 1.12 in 0.01 bands). Starting with the solution of highest specific gravity the seeds that sank were collected and separated and the remaining seeds were passed to the next solution. The resulting eight batches of seed were germinated separately using the conditions described in example 4.1 above and each batch was placed separately back into the solution in which it had sunk prior to germination. Seeds that floated were collected. Seeds that floated in specific gravity bands 1.11–1.12 and 1.10–1.11 were separated again in bands of the same specific gravity and those that floated were combined. Examination of these seeds showed that 96% had germinated and had a radicle length of 1–2 mm.

Preliminary and final drying were then carried out as described in example 4.1 above to a moisture content of 16.0%.

3. Sowing in Dutch Light Frames

Open Dutch light frames simulate the conditions of seed beds in the field. Seeds obtained in 4.2 above together with natural seeds as a control were sown in March in Dutch light frames, randomly spaced in 15 mm deep furrows. The seeds were covered with sieved soil, rolled with a "stanhay" press wheel under no additional pressure and the Dutch light frmes were left open to ambient conditions. The following results were obtained:

|  | % emergence | Time to 50% emergence (days) |
|---|---|---|
| natural seeds | 85.4 | 21.0 |
| treated seeds | 99.6 | 16.5 |

4. Sowing in Modules

Plants are generally grown in modules by specialist plant raisers for sale to other growers who transplant them into the field or glasshouse. Seeds obtained in 4.1 and 4.2 above together with natural seed as a control were sown by hand in March into "Hassy" trays with 1 seed per module. Each seed is sown into a 4 mm deep rounded depression and covered with moist vermiculite. The trays were filled with Levington transplant compost and irrigated by mist irrigation. The modules were maintained under heated glasshouse conditions with a minimum night temperature of 14° C. and a minimum day time temperature of 17° C. The following results were obtained:

|  | % emergence | Time to 50% emergence (days) |
|---|---|---|
| natural seeds | 84.5 | 6.0 |
| treated seeds (hand selection) | 99.8 | 3.5 |
| treated seeds (sucrose gradient selection) | 99.3 | 3.5 |

Example 5—Leek

Leek seeds (cv Snowstar) were germinated, selected and dried as described in example 2 above except that treatment in aerated water was carried out for 3 days and final drying was carried out for 13¾ hours. The dried seeds had a moisture content of 19.7%. The seeds were sown with natural seed as a control in modules as described in example 4.4 above except that after being coated with moist vermiculite the seeds were also covered with a layer of silver sand. The following results were obtained:

|  | % emergence | Time to 50% emergence (days) |
|---|---|---|
| natural seed | 84.1 | 12.5 |
| treated seed | 92.3 | 8.5 |

Example 6—Cauliflower

1. Seed Treatment

Cauliflower seeds (cv Snowy River) were germinated and separated as described in example 4.1 (hand separation) and 4.2 (separation on sucrose gradients). The treatment in aerated water was carried out for 3 days. Separation on sucrose gradients utilised in 5 solutions in the specific gravity range 1.08 to 1.13 in bands of 0.01. The seeds separated by sucrose graidents were found to be 98% germinated and to have radicles less than 2.5 mm in length. Preliminary and final drying were carried out in each case as described in example 2 above, final drying being carried out for 5½ hours to a moisture content of 16.8%.

2. Sowing in Modules

Seeds treated in accordance with 6.1 above were sown in March together with natural seed as controls in modules as described in 4.4 above. The following results were obtained:

|  | % emergence | Time to 50% emergence (days) |
|---|---|---|
| natural seed | 94.1 | 6.5 |
| treated seed (hand selection) | 99.0 | 5.0 |
| treated seed (sucrose gradient selection) | 99.4 | 5.0 |

Example 7—Rape

1. Seed Treatment

Rape seeds (cv Bienvenue) were germinated and separated as described in example 4.2 (separation on sucrose gradients). The treatment in aerated water was carried out for 2 days. Separation on sucrose gradients utilised 5 solutions in the specific gravity range less than 1.05 to 1.09 in bands of 0.01. The seeds which following treatment in aerated water floated in the bands 1.05 to 1.08 were combined and found to be 97% germinated and to have radicles with a length in the range 1.2 mm. Preliminary and final drying were carried out in each case as described in example 2 above for 5½ hours to a moisture content of 13.1%.

2. Sowing in Dutch Light Frames

Seeds treated in accordance with example 7.1 above were sown in March together with natural seed as control in open Dutch light frames as described in 4.3 above. The following results were obtained:

|  | % emergence | Time to 50% emergence (days) |
|---|---|---|
| natural seed | 91.5 | 17.0 |
| treated seed | 99.0 | 13.0 |

What is claimed:

1. A high viability seed lot of a plant species other than one characterised by a seminal root system, said seeds having been selected on the basis of having an emerged radicle and said seeds having a moisture content at which radicle development is suspended without loss of seed viability.

2. The seed lot according to claim 1 wherein said seeds are of a species of the genus Brassica, Allium, or Beta.

3. The seed lot according to claim 1 wherein said seeds are of a small seeded vegetable.

4. The seed lot according to claim 1, wherein said seeds have been coated.

5. A process for the production of a high viability seed lot from seeds of a plant species other than one characterised by a seminal root system which comprises germinating said seeds to a stage where radicles have emerged in a substantial proportion thereof, selecting those seeds having emerged radicles and drying said seeds under conditions and to a moisture content which suspends radicle development but does not result in loss of viability.

6. The process according to claim 5 wherein said seeds are subjected to a two stage drying process said first stage comprising drying said seeds to a moisture content at which individual seeds are separable and free flowing and said second stage comprising further drying said seeds under conditions and to a moisture content which suspend radicle development but do not result in loss of viability.

7. The process according to claim 6 wherein said second stage drying is carried out by exposing said germinated seed to a drying atmosphere of fairly high relative humidity, at a temperature in the range 20° to 30° C.

8. The process according to claim 7 wherein said drying atmosphere has a relative humidity of 70% to 90%.

9. The process according to claim 5 wherein said seeds are coated before or after final drying to facilitate handling and sowing without damage.

10. The process according to claim 5 wherein said seeds are of a species of the genus Brassica, Allium, or Beta.

11. The process according to claim 5 wherein said seeds are of a small seeded vegetable.

* * * * *

US004905411B1

REEXAMINATION CERTIFICATE (4067th)

United States Patent [19]

Finch-Savage

[11] B1 4,905,411

[45] Certificate Issued May 2, 2000

[54] SEED TREATMENT

[75] Inventor: William E. Finch-Savage, Kineton, United Kingdom

[73] Assignee: British Technology Group Limited, London, United Kingdom

Reexamination Request:
No. 90/005,352, May 10, 1999

Reexamination Certificate for:
| | |
|---|---|
| Patent No.: | 4,905,411 |
| Issued: | Mar. 6, 1990 |
| Appl. No.: | 07/300,686 |
| Filed: | Jan. 19, 1989 |

Related U.S. Application Data

[63] Continuation of application No. 07/229,459, Aug. 8, 1988, abandoned, which is a continuation of application No. 06/863,949, May 16, 1986, abandoned.

[30] Foreign Application Priority Data

| May 16, 1985 | [GB] | United Kingdom | 8512391 |
|---|---|---|---|
| May 17, 1985 | [GB] | United Kingdom | 8512586 |
| Sep. 23, 1985 | [GB] | United Kingdom | 8523448 |
| Oct. 31, 1985 | [GB] | United Kingdom | 8526823 |

[51] Int. Cl.$^7$ ........................................ A01C 1/00
[52] U.S. Cl. ............................ 47/58.1; 47/DIG. 9
[58] Field of Search ................................ 47/58.1

[56] References Cited

U.S. PATENT DOCUMENTS

| 1,756,497 | 4/1930 | Warren . |
|---|---|---|
| 2,789,398 | 4/1957 | Willett . |
| 2,954,643 | 10/1960 | Porter et al. . |
| 3,130,694 | 4/1964 | Gatzke . |
| 3,905,152 | 9/1975 | Loperfido ............................ 47/57.6 |
| 3,950,892 | 4/1976 | Simkin . |
| 4,315,380 | 2/1982 | Davidson . |
| 4,467,560 | 8/1984 | Simak . |
| 4,631,860 | 12/1986 | Broughton . |

FOREIGN PATENT DOCUMENTS

| 0030575 | 6/1981 | European Pat. Off. . |
|---|---|---|
| 0062383 | 10/1982 | European Pat. Off. . |
| 0171553 | 2/1986 | European Pat. Off. . |
| 2270773 | 12/1975 | France . |
| 1964001 | 6/1971 | Germany . |
| 2736407 | 2/1979 | Germany . |
| 1136758 | 1/1985 | U.S.S.R. . |
| 268291 | 8/1927 | United Kingdom . |
| 926856 | 5/1963 | United Kingdom . |
| 1470133 | 4/1977 | United Kingdom . |
| 1492438 | 11/1977 | United Kingdom . |
| 1535926 | 12/1978 | United Kingdom . |
| 1583148 | 1/1981 | United Kingdom . |
| 2064941 | 6/1981 | United Kingdom . |

OTHER PUBLICATIONS

Nemmer et al, "Survival of Dehydrated Pea Seedlings," Biodynamica, No. 146, pp. 193–211 (1954).
Saussure, T., "Concerning the Influence of Drying on the germination of various food seeds," (Given to Geneva Physics and Natural History Society on Mar. 17, 1825), pp. 68–93.
Dasgupta et al, "Desiccation–Tolerant and Desication–Intolerant Stages . . . ," Journal of Experimental Botany, vol. 33, p. 1045–1047 (1977).
Hegarty, T.W., "Seed Activation and Seed Germination . . . ," New Phytologist, vol. 78, pp. 349–359 (1977).
Watt, L.A., "The Effect of Water Potential on the Germination . . . ," Soil Conservation Journal, vol. 29, pp. 28–41 (1974).
Carceller et al, "Effect of Treatments Given to Grain on the . . . ," Canadian Journal of Botany, vol. 50, pp. 105–108 (1971).
Hubac, C., "La 'Riviviscence' Ou Aptitude a L'Anhydroboise' Et . . . ," Arid Zone Research News Letter, vol. 16, pp. 271–274 (1962).
May et al, "Pre–Sowing Hardening of Plants to Drought," Field Crop Abstracts, vol. 15, pp. 1–6 (1962).
Hassanyar et al, "Tolerance of Desiccation in Germinating Seeds . . . ," Agronomy Journal, vol. 71, pp. 783–786 (1979).
Heydecker et al, "Invigoration of Seeds?", Seed Science & Technology, vol. 3, pp. 881–888 (1975).
S. Matthews et al, "Seed Physiology," Conference Malvern Ref. Book, pp. 70–85 (1978).
Hegarty, T.W., "The Physiology of Seed Hydration and Dehydration, and the . . . ," Plant, Cell and Environment, vol. 1, pp. 101–119 (1978).
Schopfer et al, "Control of Seed Germination by Abscisic Acid," Plant Physiology, vol. 64, pp. 822–827 (1979).
Schopfer et al, "Control of Seed Germination by Abscisic Acid," Plant Physiology, vol. 76, pp. 155–160.
McKersie et al, "Effects of Dehydration Treatments on Germination, Seeding, . . . ," Can. J. Bot., vol. 58, pp. 471–475 (1980).
"Modules," Grower, pp. 15 & 17 (1984).

(List continued on next page.)

*Primary Examiner*—Michael J. Carone

[57] ABSTRACT

The invention relates to germinated seeds of a plant species other than one characterised by a seminal root system, for example seeds of small seeded vegetables, the seeds having emerged radicles and a moisture content at which radicle development is suspended without loss of seed viability. Seeds may be subjected to a treatment which includes imbibing the seeds to a stage where radicles have emerged in a substantial proportion thereof and drying in a two stage process the first stage comprising drying to a moisture content at which individual seeds are separable and free flowing and the second stage comprising drying in an atmosphere of fairly high relative humidity such as 70% to 90% at a temperature in the range 20° to 30° C.

Seeds treated according to the invention have advantageous properties in terms of storage and subsequent development on exposure to a suitable environment.

OTHER PUBLICATIONS

Berrie et al, "The Effect of Hydration–Dehydration," New Phytol, vol. 70, pp. 135–142 (1971).

Finch–Savage and McQuistan, NVRS Annual Report (1983).

Siminovitch et al, "Drought and Freezing Tolerance and Adaptation . . . ," Cryobiology, vol. 20, pp. 487–503 (1983).

Siminovitch et al, "Twenty–Four–Hour Induction of Freezing . . . ," Plant Physiol, vol. 69, pp. 250–255 (1982).

Hassanyar et al, "Tolerance of Desiccation in Geminating Seeds . . . ," Agronomy Journal, vol. 71, pp. 783–786 (1979).

Waisel, Y., "Presowing Treatments and Their Relation to Growth . . . ," Physiologia Planarum, vol. 15, pp. 43–46 (1962).

Milthorpe, F. L., "Changes in the Drought Resistance of Wheat Seedlings . . . ," Annals of Botany, vol. XIV, pp. 79–89 (1940).

Fluid Drilling, Ltd., "Variations on the Basic Principles."

Walter, E., "Effektivitat Der Saatgutvorbehandlung im . . . ," Gartenbau, vol. 1, pp. 3–5 (1986).

Hagner, M., "Forgrodda Fron," Sveriges Shogsvadsforbunds Tidskrift, vol. 1, pp. 57–63 (1985).

REEXAMINATION CERTIFICATE ISSUED UNDER 35 U.S.C. 307

THE PATENT IS HEREBY AMENDED AS INDICATED BELOW.

Matter enclosed in heavy brackets [ ] appeared in the patent, but has been deleted and is no longer a part of the patent; matter printed in italics indicates additions made to the patent.

AS A RESULT OF REEXAMINATION, IT HAS BEEN DETERMINED THAT:

Claims 1 and 5 are determined to be patentable as amended.

Claims 2, 3, 4, 6, 7, 8, 9, 10 and 11, dependent on an amended claim, are determined to be patentable.

New claims 12, 13, 14, 15, 16, 17, 18, 19, 20 and 21 are added and determined to be patentable.

1. A high viability seed lot of a plant species other than one characterised by a seminal root system, said seeds having been selected on the basis of having an emerged radicle and [said seeds] having a moisture content at which radicle development is suspended without loss of seed viability, *the seed lot being such that when sown the time to 50% emergence is less than that for a natural ungerminated seed lot of the same seed sown under the same conditions.*

5. A process for the production of a high viability seed lot from seeds of a plant species other than one characterised by a seminal root system which comprises germinating said seeds to a stage where radicles have emerged in a substantial proportion thereof, selecting those seeds having emerged radicles and drying said seeds under conditions and to a moisture content which suspends radicle development but does not result in loss of viability, *the seed lot being such that when sown the time to 50% emergence is less than that for a natural ungerminated seed lot of the same seed sown under the same conditions.*

*12. A high viability seed lot according to claim 1 wherein the seed is capable of continuing normal developemnt on sowing.*

*13. A high viability seed lot according to claim 1 said seeds having a moisture content of 20% or less calculated on a fresh weight basis such that the water content is that at which radicle development is suspended without loss of seed viability.*

*14. A high viability seed lot according to claim 1 said seeds having a moisture content of 20% or less calculated on a fresh weight basis such that the water content is that at which radicle development is suspended without loss of seed viability wherein when sown 92.3% or more of the seeds proceed to emergence and the time of 50% emergence is 2 or more days less than that for a natural ungerminated seed lot of the same seed sown under the same conditions.*

*15. A process according to claim 6 wherein the drying includes exposing the seeds in the first and/or second stage to air moving at a rate sufficient to assist evaporation of water from the seed.*

*16. A process according to claim 5 wherein the drying comprises treating the seed with a liquid medium which is physiologically inert, to which the germinated seeds are impermeable and which has an osmotic strength such that moisture passes from the seed to the liquid medium.*

*17. A process according to claim 5 wherein the drying comprises treating the seed with an aqueous solution of polyethylene glycol (PEG) which has an osmotic strength such that moisture passes from the seed to the liquid medium.*

*18. A high viability seed lot according to claim 1 wherein when sown 99% or more of the seeds proceed to emergence.*

*19. A process according to claim 5 wherein when sown 99% or more of the seeds proceed to emergence.*

*20. A process according to claim 5 wherein the seed lot is stored at about ±3° C.*

*21. A process according to claim 5 wherein said seeds are sown in seed trays.*

* * * * *